United States Patent
Huh

(10) Patent No.: US 7,308,719 B2
(45) Date of Patent: Dec. 18, 2007

(54) FRONT SURFACE OPENED WELDING MASK

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 65 days.

(21) Appl. No.: 11/396,803

(22) Filed: Apr. 3, 2006

(65) Prior Publication Data

US 2007/0079417 A1    Apr. 12, 2007

(30) Foreign Application Priority Data

Oct. 7, 2005    (KR) ............ 20-2005-0028622

(51) Int. Cl.
*A61F 9/06*    (2006.01)
(52) U.S. Cl. .......................................... 2/8.2
(58) Field of Classification Search ........ 2/8.1, 2/8.2–8.8, 441, 453, 429; 219/147; 359/892
See application file for complete search history.

(56) References Cited

U.S. PATENT DOCUMENTS

| | | | | |
|---|---|---|---|---|
| 3,251,065 A * | 5/1966 | Caldwell | ........ | 2/8.3 |
| 4,774,723 A * | 10/1988 | Ruck | ........ | 2/8.1 |
| 4,853,973 A * | 8/1989 | Boochard | ........ | 2/8.1 |
| 5,140,707 A * | 8/1992 | Johnson | ........ | 2/8.1 |
| 5,533,206 A * | 7/1996 | Petrie et al. | ........ | 2/8.5 |
| D393,933 S | 4/1998 | Huh | ........ | D29/110 |
| 6,185,739 B1 * | 2/2001 | Verkic et al. | ........ | 2/8.1 |
| D446,887 S | 8/2001 | Young | ........ | D29/107 |
| 6,401,244 B1 * | 6/2002 | Kramer et al. | ........ | 2/8.1 |
| D478,111 S | 8/2003 | Huh | ........ | D16/312 |
| D481,832 S | 11/2003 | Huh | ........ | D29/110 |
| D482,502 S | 11/2003 | Huh | ........ | D29/110 |
| D482,503 S | 11/2003 | Huh | ........ | D29/110 |
| 6,973,672 B2 | 12/2005 | Huh | ........ | 2/8 |
| 2003/0033661 A1 | 2/2003 | Huh | ........ | 2/436 |

OTHER PUBLICATIONS

U.S. Appl. No. 11/053,977, filed Feb. 9, 2005, USPTO Filing Receipt 15448020, Confirmation No. 8527, Applicant: Moon Young Huh, Projected Publication Date: Aug. 10, 2006.
U.S. Appl. No. 11/054,230, filed Feb. 9, 2005, USPTO Filing Receipt 15448424, Confirmation No. 9444, Applicant: Moon Young Huh, Projected Publication Date: Apr. 20, 2006.

* cited by examiner

*Primary Examiner*—Danny Worrell
(74) *Attorney, Agent, or Firm*—Cantor Colburn LLO

(57) ABSTRACT

A front surface opened welding mask, in which an LCD shielding screen is simply attached to and detached from a welding plane and the LCD shielding screen is safely connected to the welding plane. The front surface opened welding mask includes a connection opening formed through the front surface of the welding plane, a front cover having a transparent window formed through the central portion thereof and attached to and detached from the connection opening, and buttons for connecting the front cover to the connection opening. The front cover having the transparent window is easily attached to and detached from the connection opening of the welding plane so that the LCD shielding screen is simply attached to and detached from the welding plane and a receiving portion fixes the LCD shielding screen without movement so that the LCD shielding screen is safely connected to the welding plane.

3 Claims, 4 Drawing Sheets

FRONT SURFACE OPENED WELDING MASK

BACKGROUND OF THE INVENTION

1. Field of the Invention

The present invention relates to a welding mask put on by a user during a welding process for protecting user's eyes and face, and more particularly to a welding mask employing a connecting structure of an LCD shielding screen, in which the LCD shielding screen is easily attached to and detached from a welding plane of the welding mask and the LCD shielding screen is safely connected to the welding plane.

2. Description of the Related Art

Generally, various welding operations generate several dangers, such as strong harmful rays and splashing of base metal onto a user's face due to momentary heat of a high temperature and resistance. Accordingly, it is well known that a welding mask for protecting user's eyes and face from the above dangers during welding is used.

As shown in FIG. 1, a welding mask comprises a welding plane 10 having a transparent window 12 formed through the front surface thereof for covering a user's whole face, a wearable band 20 put on by a user at his/her head and connected to the welding plane 10 using a rotary shaft 22 for rotating the welding plane 10 up and down at a designated angle, and an LCD shielding screen 30 installed in the rear of the transparent window 12 of the welding plane 10 for protecting user's eyes from harmful rays generated from a welding operation.

The LCD shielding screen 30 comprises an LCD panel installed in a case for allowing a user to look outside therethrough and shielding harmful rays, a control unit for detecting the harmful rays generated during welding to operate the LCD panel, and a power supply unit for supplying power to the LCD panel and the control unit.

Accordingly, the LCD shielding screen 30 contacts the rear surface of the transparent window 12 of the welding plane 10, as described above, and is simultaneously fixed to the welding plane 10 using bolts so that the LCD shielding screen 30 is not easily detached from the welding plane 10.

The above-mentioned connecting structure of the LCD shielding screen 30 to the welding plane 10 of the welding mask causes an inconvenience in replacing the LCD shielding screen 30 with a new one. That is, when the LCD shielding screen 30, which is damaged, needs to be replaced with a new one or the transparent window 12 of the welding plane 10, which is used for a long time, needs to be replaced with a new one, the LCD shielding screen 30 must be separated from the welding plane 10, thereby causing an inconvenience in loosening and fastening a plurality of the bolts. Accordingly, an improved connecting structure of an LCD shielding screen for a welding mask has been required.

SUMMARY OF THE INVENTION

Therefore, the present invention has been made in view of the above problems, and it is an object of the present invention to provide a front surface opened welding mask, in which an LCD shielding screen is easily attached to and detached from a welding plane of the welding mask and the LCD shielding screen is safely connected to the welding plane.

It is another object of the present invention to provide a front surface opened welding mask, in which a worker can easily and conveniently replace an LCD shielding screen with a new one.

In accordance with the present invention, the above and other objects can be accomplished by the provision of a front surface opened welding mask, to which an LCD shielding screen is connected, to protect user's eyes from strong harmful rays generated during welding, comprising: a connection opening formed through the central portion of a welding plane and provided with a receiving portion formed along the edge thereof so that the LCD shielding screen is mounted on the connection opening, said receiving portion comprising a latching protrusion formed on the lower side surface thereof and connection spaces, each having opened front and left or right portions, formed at both sides of the upper side surface thereof; a front cover comprising a transparent window connected to the central portion thereof, a latching groove formed in the lower side surface thereof correspondingly to the latching protrusion, and connection pieces, each having a connection hole, formed on the upper side surface thereof and connected to the corresponding connection spaces; and buttons, inserted into the corresponding connection spaces, each comprising an elastic member formed therein, bent in a zigzag shape, and exerting designated elastic force, a hook protrusion formed on the central portion thereof and inserted into the connection hole of the corresponding one of the connection pieces, and a press portion formed on the outer surface thereof and pressed by a user's hand for separating the hook protrusion from the connection hole of the connection piece.

Preferably, supporters for fixedly supporting the LCD shielding screen may be formed on the upper and lower side surfaces of the receiving portion.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, a preferred embodiment of the present invention will be described in detail with reference to the annexed drawings.

Figure 1:
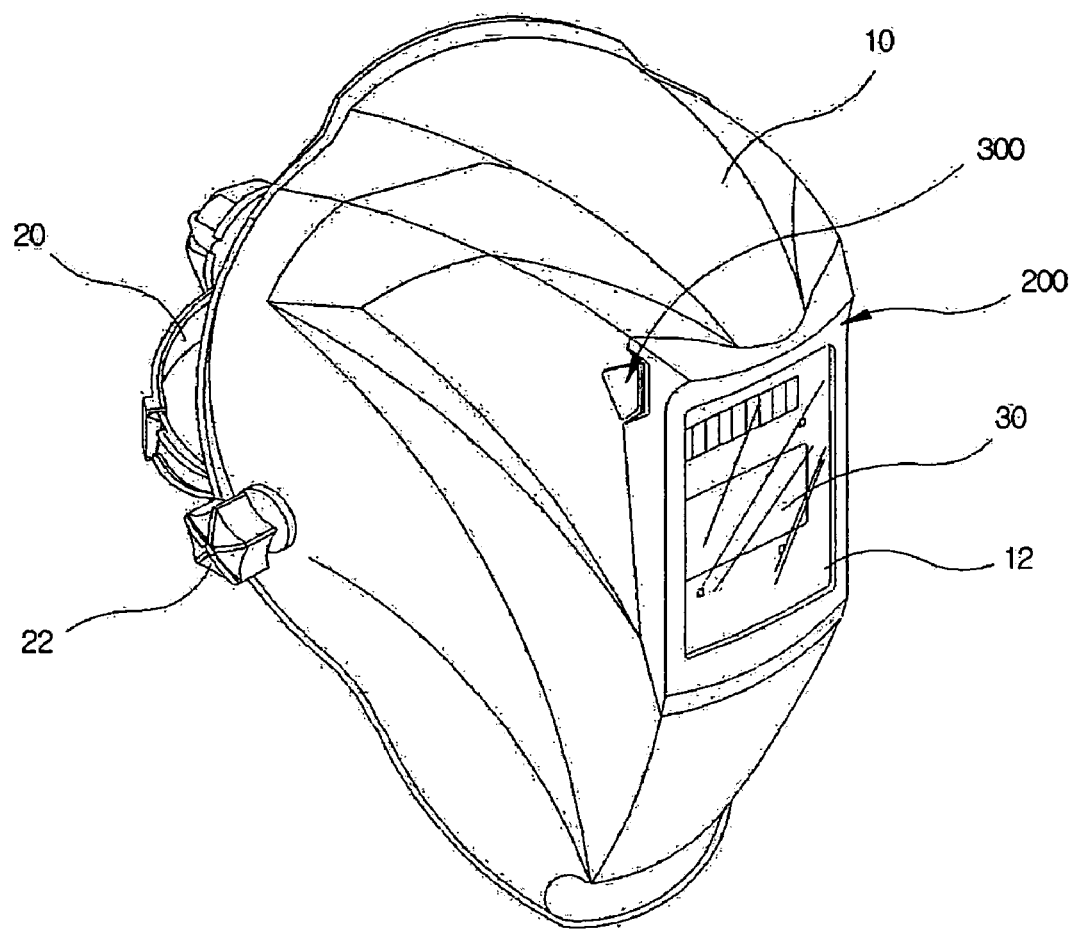
FIG. 1 is an assembled perspective view of a front surface opened welding mask in accordance with a preferred embodiment of the present invention.
Figure 2:
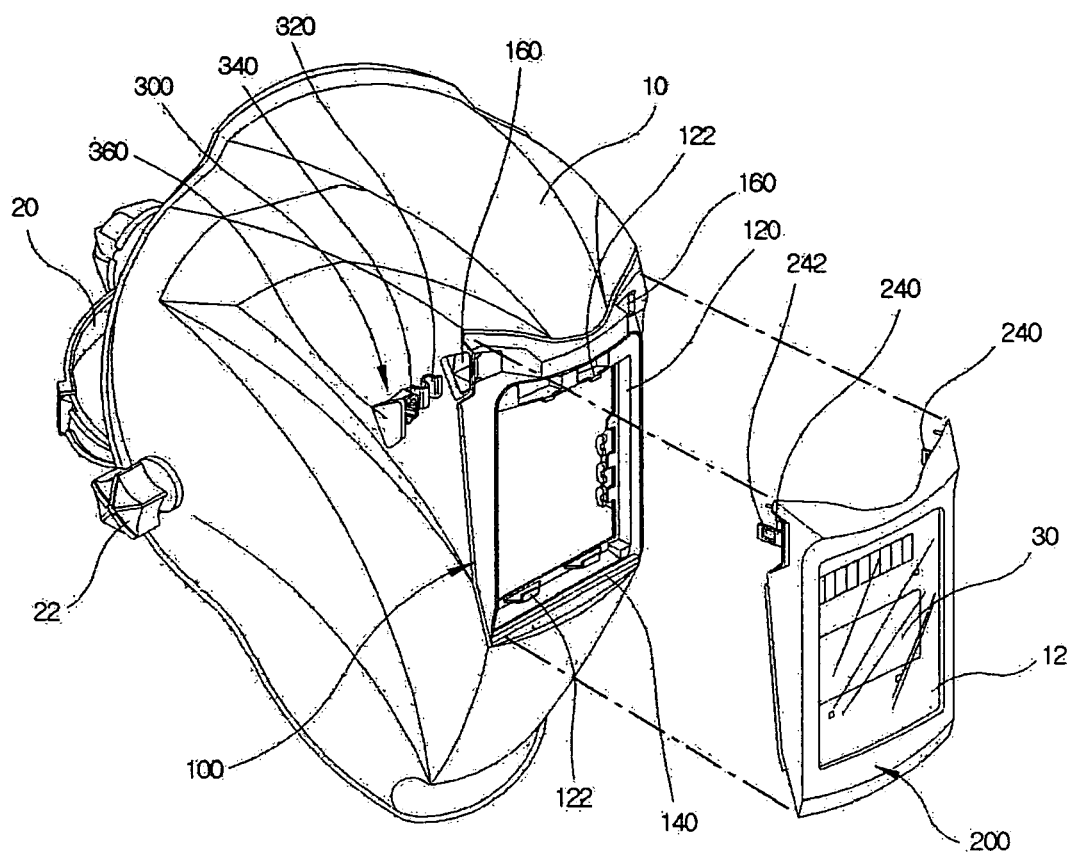
FIG. 2 is an exploded perspective view of the front surface opened welding mask in accordance with the preferred embodiment of the present invention.
Figure 3:
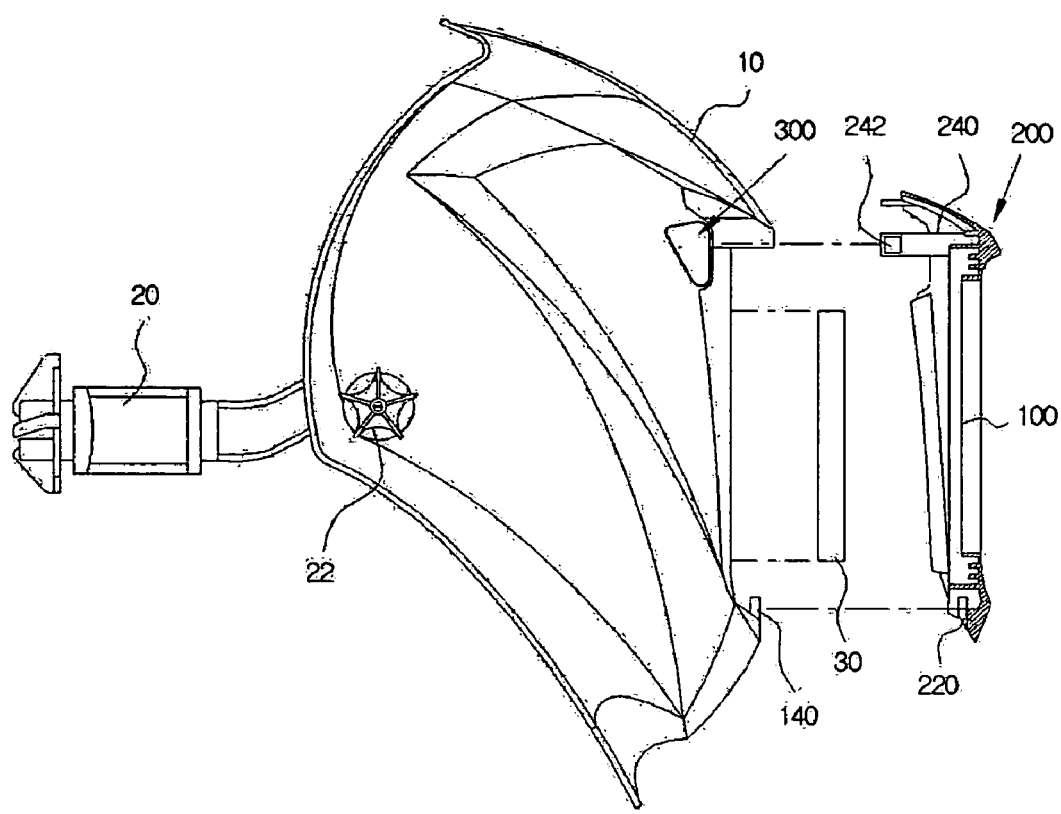
FIG. 3 is an exploded side view of the front surface opened welding mask in accordance with the preferred embodiment of the present invention.
Figure 4:
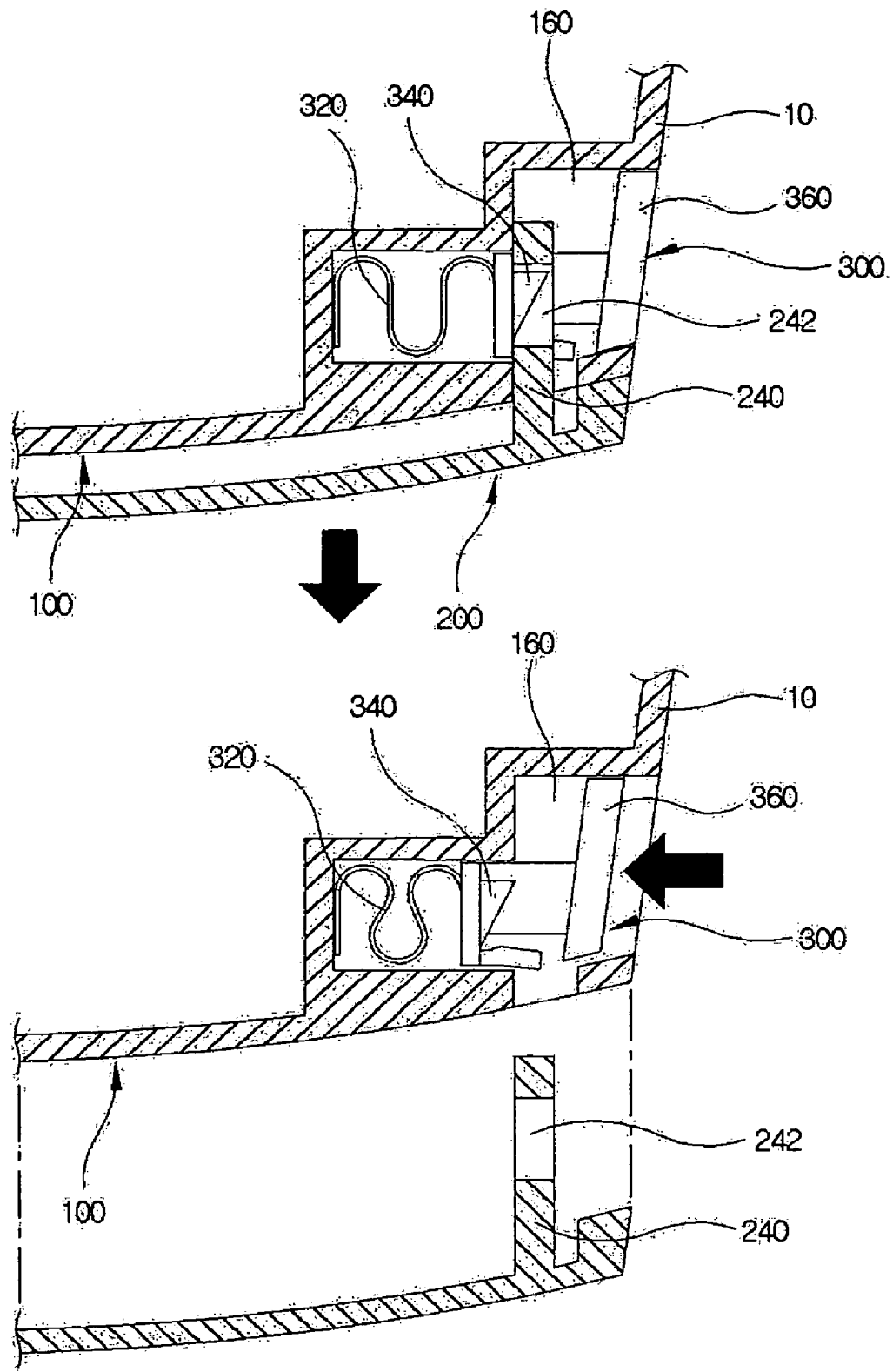
FIG. 4 is a sectional view of an essential portion of the front surface opened welding mask in accordance with the preferred embodiment of the present invention.

FIG. 1 is an assembled perspective view of a front surface opened welding mask in accordance with a preferred embodiment of the present invention, FIG. 2 is an exploded perspective view of the front surface opened welding mask in accordance with the preferred embodiment of the present invention, FIG. 3 is an exploded side view of the front surface opened welding mask in accordance with the preferred embodiment of the present invention, and FIG. 4 is a sectional view of an essential portion of the front surface opened welding mask in accordance with the preferred embodiment of the present invention.

As shown in FIGS. 1 to 4, the front surface opened welding mask of the present invention comprises a connection opening 100 formed through the front surface of a welding plane 10, a front cover 200 having a transparent window 12 formed through the central portion thereof and attached to and detached from the connection opening 100, and buttons 300 for connecting the front cover 200 to the connection opening 100.

Identically with the conventional welding mask, the front surface opened welding mask of the present invention further comprises the welding plane 10 having the transparent window 12 formed through the front surface thereof for covering a user's whole face, a wearable band 20 put on by a user at his/her head and connected to the welding plane 10 using a rotary shaft 22 for rotating the welding plane 10 up and down at a designated angle, and an LCD shielding screen 30 installed in the rear of the transparent window 12 of the welding plane 10 for protecting user's eyes from harmful rays generated from a welding operation.

The LCD shielding screen 30 comprises an LCD panel installed in a case for allowing a user to look outside therethrough and shielding harmful rays, a control unit for detecting the harmful rays generated during welding to operate the LCD panel, and a power supply unit for supplying power to the LCD panel and the control unit.

The transparent window 12 is simply attached to and detached from the welding plane 10, and the LCD shielding screen 30 is interposed between the welding plane 10 and the transparent window 12.

A receiving portion 120 is formed along the connection opening 100 formed through the front surface of the welding plane 10 so that the LCD shielding screen 30 is connected to the receiving portion 120. Supporters 122, to which the LCD shielding screen 30 is fixed, are installed on the upper and lower side surfaces of the receiving portion 120. That is, the supporters 122 are simply unfolded so that the LCD shielding screen 30 can be separated from the receiving portion 120.

A latching protrusion 140, which corresponds to a latching groove 220 formed in the lower side surface of the front cover 200, is protruded from the lower side surface of the receiving portion 120. Connection spaces 160, each having opened front and left or right portions, are concaved in both sides of the upper side surface of the receiving portion 120 so that the corresponding button 300 and a corresponding one of connection pieces 240 of the front cover 200 are connected to each of the connection spaces 160. That is, the front cover 200 is simply attached to and detached from the connection opening 100 under the condition that the connection pieces 240 are inserted into the connection spaces 160.

The transparent window 12 is connected to the central portion of the front cover 200. The latching groove 220 corresponding to the latching protrusion 140 is formed in the lower side surface of the front cover 200, and the connection pieces 240, each having a designated connection hole 242, connected to the connection spaces 160 are formed on the upper side surface of the front cover 200.

Hook protrusions 340 of the buttons 300 are fixedly inserted into the connection holes 242 formed in the connection pieces 240. That is, the front cover 200 is simply attached to and detached from the connection opening 100 under the condition that the front cover 200 contacts the connection opening 100 of the welding plane 100 using the latching groove 220 and the connection pieces 240 of the front cover 200, and fixes the LCD shielding screen 30 connected to the receiving portion 120.

The buttons 300 serve to lock or unlock the corresponding connection pieces 240 of the front cover 200 by constant elastic force under the condition that the buttons 300 are connected to the right and left connection spaces 160. That is, an elastic member 320 bent in a zigzag shape and exerting designated elastic force is formed in each of the buttons 300, the hook protrusion 340 inserted into the connection hole 242 of the corresponding one of the connection pieces 240 of the front cover 200 is formed on the central portion of each of the buttons 300, and a press portion 360 pressed by a user's hand for separating the hook protrusion 340 from the connection hole 242 of the connection piece 240 is formed on the outer surface of each of the buttons 300.

Accordingly, when the connection pieces 240 are inserted into the connection spaces 160, the inserted state of the hook protrusions 340 into the connection holes 242 of the connection pieces 240 is maintained by the elastic members 320, and when the press portions 360 are pressed, the elastic members 320 are compressed and the hook protrusions 340 are separated from the connection holes 242 so that the front cover 200 can be separated from the connection opening 100.

In accordance with the above-described structure, the front cover 200 having the transparent window 12 is simply attached to and detached from the connection opening 100 of the welding plane 10 by the buttons 300, and the LCD shielding screen 30 is simply attached to and detached from the front cover 200.

As apparent from the above description, the present invention provides a front surface opened welding mask, in which a front cover having a transparent window is easily attached to and detached from a connection opening of a welding plane of the welding mask so that an LCD shielding screen is simply attached to and detached from the welding plane and a receiving portion fixes the LCD shielding screen without movement so that the LCD shielding screen is safely connected to the welding plane.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A front surface opened welding mask, to which an LCD shielding screen is connected, to protect user's eyes from strong harmful rays generated during welding, comprising:

a connection opening formed through the central portion of a welding plane and provided with a receiving portion formed along the edge thereof so that the LCD shielding screen is mounted on the connection opening, said receiving portion comprising a latching protrusion formed on the lower side surface thereof and connection spaces, each having opened front and left or right portions, formed at both sides of the upper side surface thereof;

a front cover comprising a transparent window connected to the central portion thereof, a latching groove formed in the lower side surface thereof correspondingly to the latching protrusion, and connection pieces, each having a connection hole, formed on the upper side surface thereof and connected to the corresponding connection spaces; and buttons, inserted into the corresponding connection spaces, each comprising an elastic member formed therein, bent in a zigzag shape, and exerting designated elastic force, a hook protrusion formed on the central portion thereof and inserted into the connection hole of the corresponding one of the connection pieces, and a press portion formed on the outer surface thereof and pressed by a user's hand for separating the hook protrusion from the connection hole of the connection piece.

2. The front surface opened welding mask as set forth in claim 1, wherein supporters for fixedly supporting the LCD shielding screen are formed on the upper and lower side surfaces of the receiving portion.

3. The front surface opened welding mask as set forth in claim 1, wherein the elastic member, the hook protrusion, and the press portion of each of the buttons are integrally molded so that the buttons can exert elastic force.

* * * * *